(12) United States Patent
Smith, Jr. et al.

(10) Patent No.: US 6,583,325 B1
(45) Date of Patent: Jun. 24, 2003

(54) PROCESS FOR THE PRODUCTION OF TERTIARY ALKYL ETHERS

(75) Inventors: Lawrence A. Smith, Jr., Pasadena, TX (US); Hugh M. Putman, Houston, TX (US); Henry J. Semerak, Houston, TX (US); Clifford S. Crossland, Sarnia (CA)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 10/087,371

(22) Filed: Mar. 1, 2002

(51) Int. Cl.[7] .................................................. C07C 41/00
(52) U.S. Cl. .................................. 568/697; 203/DIG. 6
(58) Field of Search ...................... 568/697; 203/DIG. 6

(56) References Cited

U.S. PATENT DOCUMENTS

| | | | |
|---|---|---|---|
| 4,302,356 A | 11/1981 | Smith, Jr. .................... | 252/426 |
| 4,307,254 A | 12/1981 | Smith, Jr. .................... | 568/697 |
| 4,336,407 A | 6/1982 | Smith, Jr. .................... | 568/697 |
| 4,950,803 A | 8/1990 | Smith, Jr. et al. ........... | 568/697 |
| 5,258,560 A * | 11/1993 | Marker ....................... | 568/697 |
| 6,232,509 B1 | 5/2001 | Smith, Jr. et al. ........... | 568/697 |

* cited by examiner

*Primary Examiner*—Rosalynd Keys
(74) *Attorney, Agent, or Firm*—Kenneth H. Johnson

(57) ABSTRACT

A process for the production of tertiary ethers from the reaction of isoolefins with lower alcohols, such as methanol, uses two distillation column reactors in series to maximize conversion, especially for isopentenes and isohexenes. The second distillation column reactor may be concurrently used as a $C_5$ polishing reactor and a reactor for producing MTBE or ETBE from isobutene, for example.

5 Claims, 1 Drawing Sheet

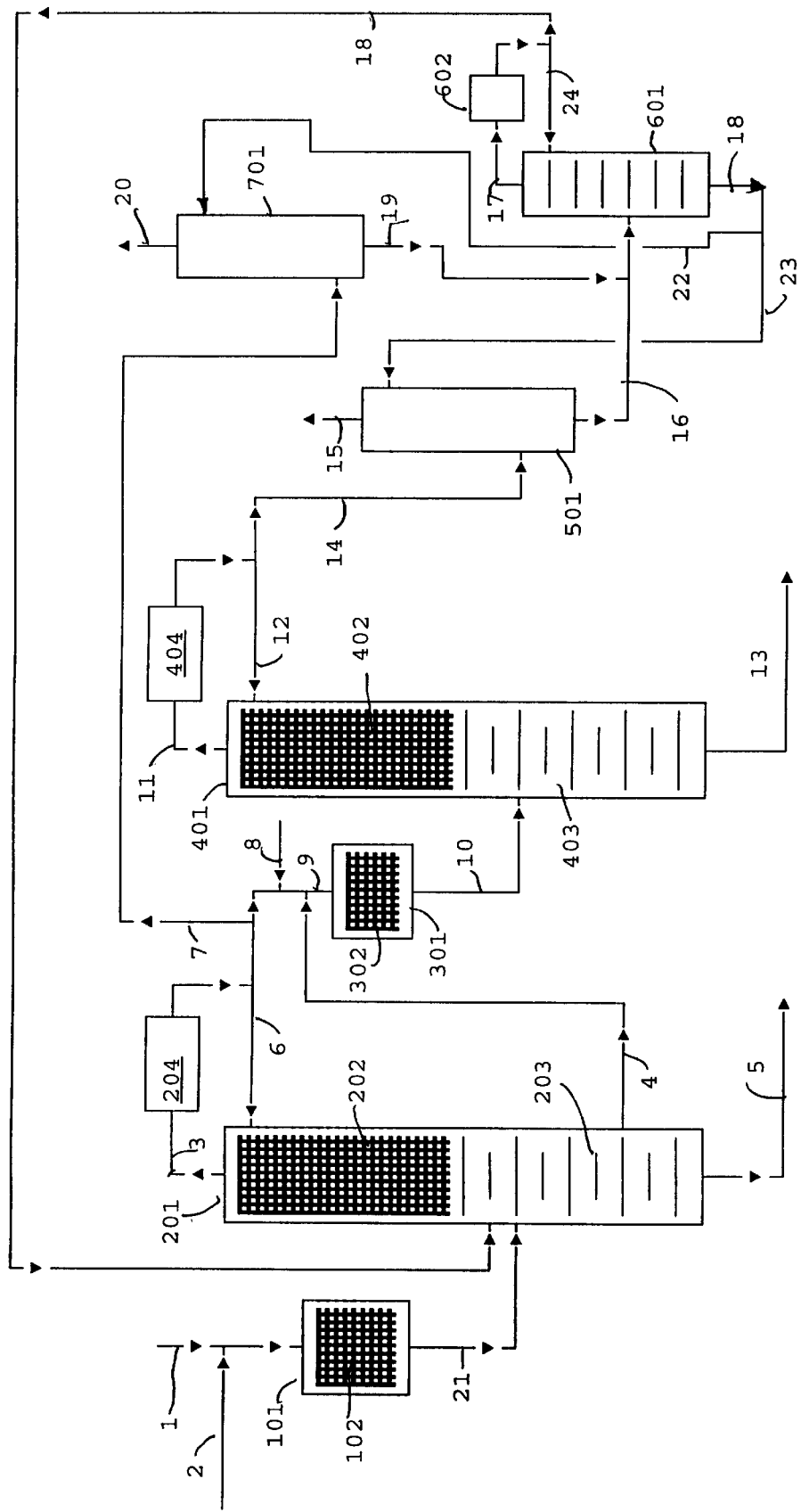

PROCESS FOR THE PRODUCTION OF TERTIARY ALKYL ETHERS

BACKGROUND OF THE INVENTION

1. Field of the Invention

The present invention relates to an integrated process to produce tertiary alkyl ethers from a $C_4$ stream and a $C_5$–$C_6$ refinery cut, more particularly the upgrading of the isoolefins to useful octane improvers, specifically by the production of methyl tertiary butyl ether (MTBE) from the reaction of isobutene with methanol, tertiary amyl methyl ether (TAME) from the reaction of isoamylenes ($iC_5^=$'s) with methanol, and tertiary hexyl methyl ether (THEME) from the reaction of isohexenes with methanol in the presence of an acid cation exchange resin.

2. Related Information

The light naphtha refinery cut is valuable as a gasoline blending stock or as source of isoolefins ($iC_5^=$'s and $iC_6^=$'s) and to form an ether by reaction with lower alcohols. The Clean Air Act and regulations implementing it require the reformulation of gasoline. Requirements for reformulated gasolines include the reduction of benzene and olefins. The reformulation has resulted in the loss of octane in the straight gasoline. Other requirements are (1) to include a certain amount of "oxygenates", such as methyl tertiary butyl ether (MTBE), TAME, tertiary hexyl methyl ether (THEME), ethyl tertiary butyl ether (ETBE) or ethanol, (2) to reduce the amount of olefins and aromatics in gasoline, and (3) to reduce the vapor pressure (volatility). Refiners have elected to meet these federal mandates by preferably using the ethers. The demand for MTBE in some areas has out stripped the available isobutene. Some refiners are looking to the $C_5$ and $C_6$ cuts which contain suitable isopentene and isohexene for producing TAME and THEME. In addition to improving air quality by adding the ether rather than the raw ethanol, which has a somewhat higher volatility, and removing the olefins, the replacement of the pentenes and hexenes with the ethers results in an increase in the octane rating of the stream.

The $C_4$'s used for feed to an MTBE unit are easily separated from the hydrocarbon source and usually contain $iC_4=$, $nC_4=$'s and some normal isobutane.

The $C_5$'s and $C_6$'s in the feed to a TAME/THEME unit are contained in a single "light naphtha" cut which contains everything from $C_5$'s through $C_8$'s and higher. This mixture can easily contain 150 to 200 components and thus identification and separation of the products are difficult. For this reason the TAME/THEME produced from these streams is not generally separated from the heavier components, but all are used directly as octane blending stocks.

Mixed refinery streams often contain a broad spectrum of olefinic compounds. This is especially true of products from either catalytic cracking or thermal cracking processes. Refinery streams are usually separated by fractional distillation, and because they often contain compounds that are very close in boiling points, such separations are not precise. A $C_5$ stream, for instance, may contain $C_4$'s and up to $C_8$'s. These components may be saturated (alkanes), unsaturated (mono-olefins), or poly-unsaturated (diolefins). Additionally, the components may be any or all of the various isomers of the individual compounds.

In most light naphtha cuts the isoamylenes and isohexenes suitable for the production of TAME/THEME are frequently present in small quantities, e.g. less than 15%, whereas there are other $C_5/C_6$ olefins isomers and enough dienes and acetylenes to inhibit the etherification process. In the present process the valuable ether production is maximized while removing olefins and other impurities found in the $C_5$ cuts. It is an advantage of the present process that the production of TAME/THEME from $C_5$–$C_6$ cuts is maximized. It is a particular feature of the present invention that the treated components can be reblended with the raffinate of the $C_5$ and $C_6$ cuts to provide an upgraded gasoline blending stream. It is a further advantage of the present invention that the raffinate stream is substantially upgraded by the reduction of olefinic content.

SUMMARY OF THE INVENTION

Briefly the present invention comprises the steps of feeding methanol and a stream containing $iC_5=$'s and $iC_6=$'s to a first distillation column reactor containing an acidic catalyst wherein a portion of the $iC_5=$'s and $iC_6=$'s are reacted to produce TAME and THEME. Simultaneously the TAME, THEME and unreacted $C_6$'s are removed as bottoms while unreacted $C_5$'s (including unreacted $C_5=$'s) and methanol are removed as overheads. The unreacted $C_5$'s and methanol are fed along with isobutene and additional methanol to a second distillation column reactor where additional $iC_5=$'s are reacted with methanol to produce additional TAME and the isobutene is reacted to produce MTBE. Unreacted $C_5$'s, TAME and MTBE are removed as bottoms while unreacted $C_4$'s and methanol are removed as overheads.

BRIEF DESCRIPTION OF THE DRAWING

The FIGURE is a simplified flow diagram of one embodiment of the invention.

DETAILED DESCRIPTION OF THE INVENTION

Glossary

For clarification purposes definitions of the following terms and abbreviations are provided:

FCC —fluid catalytically cracked or from a refinery fluid catalytic cracker.

$iC_4$—isobutane $nC_4$—normal butane $iC_4=$—isobutene $iC_5$'s—the various isomers of saturated five carbon hydrocarbons.

$nC_5$—normal pentane.

$iC_5^=$'s—the various isomers of unsaturated five carbon hydrocarbons having one double bond.

$nC_5^=$—normal pentene.

$iC_6=$—the various isomers of unsaturated six carbon hydrocarbon having one double bond.

MTBE—methyl tertiary butyl ether which is the reaction product of isobutene and methanol.

ETBE—ethyl tertiary butyl ether which is the reaction product of isobutene and ethanol.

TAME—tertiary amyl methyl ether which is the reaction product of the various $iC_5^=$ isomers with methanol.

THEME—tertiary hexyl methyl ether which is the reaction product of the various $iC_6=$ isomers with methanol.

Process

The streams useful in the present invention may be derived from any source. Generally the feeds are $C_4$–$C_6$ hydrocarbons with branched olefins present, typically with a concentration of 20% of branched olefins. Typically diolefins have been removed from these streams along with sulfur containing compounds.

The use of a fixed bed boiling point reactor in conjunction with a distillation column for etherifications is known in the art. However, some compounds have very low equilibrium conversion, e.g., THEME and TAME. Prior to this invention the solution to increase conversion has been to increase the internal reflux within the distillation column reactor. The present invention increases conversion, especially for TAME, by utilizing a second distillation column reactor.

Although highly desirable, the fixed bed etherification units are not required to carry out the process and only the distillation reactors may be used. The fixed bed etherification reactor is preferably operated as a "boiling point reactor" as described in U.S. Pat. No. 4,950,803 which is incorporated herein by reference. That is, the pressure of the fixed bed reactor is adjusted such that the reaction mixture is boiling. This conveniently removes the heat produced by the exothermic reaction as latent heat of vaporization aiding in preventing an increase in the temperature.

The unreacted methanol is removed, if desired, from the other unreacted material in the overheads from the second distillation column reactor by water washing and subsequent distillation of the methanol water mixture. The recovered methanol may be recycled to the fixed bed reactor and the water to the water wash.

U.S. Pat. Nos. 5,003,124 and 4,950,803 disclose a liquid phase process for the etherification of $C_4$ and $C_5$ isoolefins with $C_1$ to $C_6$ alcohols in a boiling point fixed bed reactor that is controlled at a pressure to maintain the reaction mixture at its boiling point which may be directly attached to a catalytic distillation reactor.

The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in a combination reactor-distillation structures are described in U.S. Pat. Nos. 4,242,530; 4,250,052; 4,232,177; 4,302,356; 4,307,254; and 4,336,407 all of which are incorporated herein by reference.

For example, in this system and procedure, methanol and isoolefin (or the stream from the boiling point reactor which contains, ether, some unreacted isoolefin and methanol or make up methanol) containing stream is continuously fed to the reactor/distillation column where they are contacted in the catalytic distillation structure. The methanol preferentially reacts with isoolefin, forming TAME and THEME which are heavier than the $C_5$ and $C_6$ components of the feed and the methanol, hence it drops in the column to form the bottoms. Concurrently, the unreacted $C_5$'s and $C_6$'s (e.g., n-pentane, n-pentenes, n-hexane and n-hexenes) are lighter and form an overhead.

Catalyst

Catalysts preferred for the etherification process are cation exchange resins, which contain sulfonic acid groups, and which have been obtained by polymerization or copolymerization of aromatic vinyl compounds followed by sulfonation.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles form 0.15 mm up to about 1 mm may be employed.

The resin catalyst is loaded into the straight pass fixed bed reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred. U.S. Pat. Nos. 4,302,356, 4,443,559 and 5,730,843 disclose catalyst structures which are useful as distillation structures and are incorporated herein by reference.

EXAMPLE

Referring now to the FIGURE a simplified flow diagram of one embodiment of the invention is shown. The $C_5$–$C_6$ stream (a FCC naphtha) is fed via flow line 2 to a first boiling point reactor 101 containing a bed of etherification catalyst 102. Methanol is fed via line 1. A portion of the isoolefins contained within the naphtha feed is reacted with methanol in the reactor 101 to form TAME and THEME. The effluent from the reactor 101 in line 21 is fed to a first distillation column reactor 201 containing a bed 202 of etherification catalyst in a distillation reaction zone. Methanol is also recycled via flow line 18. More of the isoolefins in the effluent are reacted with methanol to form additional TAME and THEME in the distillation reaction zone. The unreacted $C_5$'s and methanol are stripped from the product in stripping section 203 and removed as overheads. The bottoms, containing TAME and THEME and unreacted $C_6$'s are removed via flow line 5.

The overheads are removed via flow line 3 and contain some unreacted isoamylenes along with unreacted methanol. The overheads are condensed in condenser 204 and a portion returned to the distillation column reactor 201 via flow line 6 as reflux. A small portion is removed via flow line 7 to prevent build up of unreacted $C_5$'s and to recover methanol. The remainder of the overheads is combined with a $C_4$ stream containing isobutene from flow line 9 and fed via flow line 9 to a second boiling point reactor 301 containing a bed 302 of etherification catalyst where the isoamylenes and isobutene are reacted with methanol to produce TAME and MTBE. The effluent from the second boiling point reactor is fed via flow line 10 to a second distillation column reactor 401 containing a bed 402 of etherification catalyst in a second distillation reaction zone. Substantially all of the remaining isoamylenes and isobutene is reacted with methanol to produce additional MTBE and TAME. Unreacted methanol and $C_4$'s are stripped from the product in stripping section 403 and the product MTBE and TAME along with unreacted $C_5$'s are removed as bottoms via flow line 13.

If desired a concentrated $C_6$ fraction containing isohexenes can be withdrawn from the stripping section via flow line 4 and fed to the second boiling point reactor 302 for further conversion to THEME. In that case the additional THEME would also be removed as bottoms in flow line 13.

The overheads containing unreacted $C_4$'s (mostly n-butenes and butanes) and unreacted methanol is condensed in condenser 404 with a portion of the condensed material being returned to the distillation column reactor 401 as reflux vi flow line 12. The remainder of the overheads is fed to absorber 501 where methanol is absorbed in water and removed from the bottom via flow line 16. The unabsorbed $C_4$'s are removed from the top via flow line 15 for further processing as desired.

The $C_5$ overheads in flow line 7 are likewise fed to an absorber 701 wherein the methanol is absorbed in water and removed as bottoms via flow line 19. The methanol/water in flow lines 16 and 19 are fed to a methanol stripper 601 where the methanol is separated from the water as overheads in flow line 17 and condensed in condenser 602. Some of the methanol is returned to the stripper 601 via flow line 24 with the rest being recycled to the first distillation column reactor 201 via flow line 18. Water is taken as bottoms via flow line 18 with a portion being fed to absorber 701 via flow line 22 and another portion being fed to absorber 501 via flow line 23.

The combined boiling reactors and distillation column reactors in series allow for higher conversion of the $C_5$ and $C_6$ isoolefins while producing MTBE.

The invention claimed is:

1. A process for the production of tertiary ethers comprising the steps of:
   (a) feeding a stream comprising a $C_{5-6}$ stream containing isoolefins and $C_1$–$C_6$ alcohol to a first distillation column reactor containing a first bed of etherification catalyst in a first distillation reaction zone;
   (b) concurrently in said first distillation column reactor
      (i) reacting a portion of the isoolefins with a portion of the methanol to form a tertiary ether, and
      (ii) separating the tertiary ether product from unreacted isoolefins and unreacted methanol by fractional distillation;
   (c) withdrawing the tertiary ether product from the first distillation column reactor as a first bottoms;
   (d) withdrawing the unreacted isoolefins and unreacted methanol from the first distillation column reactor as a first overheads;
   (e) feeding the first overheads and a $C_4$ stream containing isobutene to a second distillation column reactor containing a second bed of etherification catalyst in a second distillation reaction zone;
   (f) concurrently in said second distillation column reactor
      (i) reacting more of the unreacted isoolefins and said isobutene with more of the unreacted alcohol to form additional tertiary ether, and
      (ii) separating the additional tertiary ether product from unreacted isoolefins and unreacted methanol by fractional distillation;
   (g) withdrawing the additional tertiary ether product from the second distillation column reactor as a second bottoms;
   (h) withdrawing the unreacted isoolefins and unreacted alcohol from the second distillation column reactor as a second overheads.

2. The process according to claim 1 wherein the feed to the first distillation column reactor is an FCC naphtha containing $C_5$ and $C_6$ isoolefins and methanol and the product tertiary ether comprises tertiary amyl methyl ether and tertiary hexyl methyl ether and the overheads contains unreacted $C_5$ isoolefins.

3. The process according to claim 2 wherein unreacted $C_6$'s are removed in said first bottoms along with said tertiary ether product.

4. The process according to claim 2 wherein methyl tertiary butyl ether which is withdrawn in said second bottoms.

5. A process for the production of methyl tertiary butyl ether, tertiary amyl methyl ether and tertiary hexyl methyl ether comprising the steps of:
   (a) feeding a stream containing $C_5$ and $C_6$ isoolefins and methanol to a first boiling point reactor containing an etherification catalyst wherein a portion of the $C_5$ and $C_6$ isoolefins are reacted with methanol to produce a first effluent stream containing unreacted $C_5$ and $C_6$ isoolefins, unreacted methanol, tertiary amyl methyl ether and tertiary hexyl methyl ether;
   (b) feeding said first effluent stream to a first distillation column reactor containing a first bed of etherification catalyst in a first distillation reaction zone;
   (c) concurrently in said first distillation column reactor
      (i) reacting additional $C_5$ and $C_6$ isoolefins with a methanol to form additional tertiary amyl methyl ether and tertiary hexyl methyl ether and
      (ii) separating the tertiary ether products from unreacted $C_5$ isoolefins and unreacted methanol by fractional distillation;
   (d) withdrawing the tertiary ether products from the first distillation column reactor as a first bottoms;
   (e) withdrawing the unreacted $C_5$ isoolefins and unreacted methanol from the first distillation column reactor as a first overheads;
   (f) feeding the first overheads and a stream containing isobutene to a second boiling point reactor containing an etherification catalyst wherein additional $C_5$ isoolefins and isobutene are reacted with methanol to produce a second effluent containing unreacted isobutene, unreacted $C_5$ isoolefins, methyl tertiary butyl ether, tertiary amyl methyl ether and unreacted methanol;
   (g) feeding the second effluent to a second distillation column reactor containing a second bed of etherification catalyst in a second distillation reaction zone;
   (h) concurrently in said second distillation column reactor
      (i) reacting more of the unreacted isobutene and unreacted $C_5$ isoolefins with methanol to produce additional methyl tertiary butyl ether and tertiary amyl methyl ether products and
      (ii) separating the additional tertiary ether products from unreacted $C_4$'s and unreacted $C_5$ isoolefins and unreacted methanol by fractional distillation;
   (i) withdrawing the additional tertiary ether products and unreacted $C_5$'s from said second distillation column reactor as a second bottoms; and
   (j) withdrawing unreacted $C_4$'s and unreacted methanol from said second distillation column reactor as a second overheads.

* * * * *